United States Patent [19]

Deckner et al.

[11] Patent Number: 4,970,216

[45] Date of Patent: * Nov. 13, 1990

[54] SKIN TREATMENT COMPOSITION AND METHOD

[75] Inventors: George E. Deckner, Westfield; Arthur C. W. Georgalas, Leonardo, both of N.J.

[73] Assignee: Richardson Vicks, Inc., Wilton, Conn.

[ * ] Notice: The portion of the term of this patent subsequent to Jul. 11, 2006 has been disclaimed.

[21] Appl. No.: 303,911

[22] Filed: Jan. 30, 1989

Related U.S. Application Data

[63] Continuation of Ser. No. 939,388, Dec. 8, 1986, Pat. No. 4,841,267, which is a continuation-in-part of Ser. No. 840,177, Mar. 17, 1986, abandoned.

[51] Int. Cl.$^5$ .................... A61K 31/47; A61K 31/35
[52] U.S. Cl. ................................... 514/311; 514/456; 514/917; 424/94.4
[58] Field of Search .................. 514/311, 456, 917; 424/944, 164

[56] References Cited

U.S. PATENT DOCUMENTS 4,742,066  5/1988  Deckner et al. ................... 514/311

FOREIGN PATENT DOCUMENTS 1260234  1/1972  United Kingdom ............... 514/311

OTHER PUBLICATIONS

Chem. Abst. 88(22): 158266t, 1978.

Primary Examiner—John W. Rollins
Attorney, Agent, or Firm—Lerner, David, Littenberg, Krumholz & Mentlik

[57] ABSTRACT

Skin treatment compositions are provided which inhibit generation of free radicals in the skin and which include 6-hydroxy-2,5,7,8-tetramethylchroman-2-carboxylic acid, 6-ethoxy-1,2-dihydro-2,3,4-trimethyl quinoline or mixture thereof, and optionally a stabilizer for the 6-hydroxy-2,5,7,8-tetramethylchroman-2-carboxylic acid which is monoethanolamine sulfite or sodium bisulfite.

22 Claims, No Drawings

SKIN TREATMENT COMPOSITION AND METHOD

This is a continuation of application Ser. No. 06/939,388, filed 12/8/86, now U.S. Pat. No. 4,847,267, which is a Continuation-in-Part of application Ser. No. 06/840,177 filed on 3/17/86, now U.S. Pat. No. 4,762,066 issued on 5/3/88.

FIELD OF THE INVENTION

The present invention relates to improved skin treatment compositions including cosmetics which have improved skin penetrating properties and inhibit generation of free radicals in the skin which may form upon exposure to ultraviolet radiation or air pollutants, to a method for controlling free radical formation on the skin by applying such skin treatment composition to the skin, and to a method of stabilizing Vitamin E-like preparations for use in the above compositions.

BACKGROUND OF THE INVENTION

Free radical formation plays a destructive role in biological processes of living things, Pryor, W.A., Free Radicals in Biological Systems, Scientific American, Vol. 223, No. 2, pp. 70-83, August 1970, Pryor, W. A., Free Radical Pathology, Chemical and Engineering News, June 7, 1971, p. 34ff, and Harman, D., The Aging Process, Proc. Natl. Acad. Sci., U.S.A., Vol. 78, No. 11, pp 7124-7128, Nov. 1981. It has been found that exposure of human skin to ultraviolet radiation and air pollutants could result in the generation of free radicals in the exposed skin which could lead to premature aging of such skin. Accordingly, a topical skin treatment composition which could inhibit generation or deactivation of free radicals in the skin resulting from exposure to ultraviolet radiation and/or air pollutants would indeed be most a welcome addition to the skin treatment field.

Vitamin E ($\alpha$-tocopherol) which has the structure

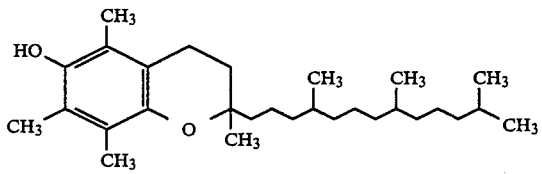

has been employed to inhibit oxidation of oils and fats in foods, cosmetic preparations and drugs and for its soothing and antiinflammatory properties. It has also been found that a number of 6-hydroxychromans, including rac-6-hydroxy2,5,7,8-tetramethylchroman-2-carboxylic acid (Trolox C) which has the structure

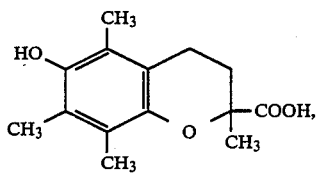

exhibit antioxidant activity (Scott et al, "Antioxidant Properties of 6-Hydroxy-2,5,7,8-tetramethylchroman-2-carboxylic acid, Cosmetics and Toiletries, Vol. 91, Nov. 1976).

DESCRIPTION OF THE INVENTION

This invention is directed to improved skin treatment compositions, including cosmetic preparations, for inhibiting generation or deactivating free radicals in the skin and which includes at least one free radical inhibitor or deactivator which is 6-hydroxy-2,5,7,8-tetramethylchroman-2-carboxylic acid (Trolox C) or 6-ethoxy-1,2-dihydro-2,2,4-trimethylquinoline (ethoxyquin) or mixtures thereof in an amount within the range of from about 0.01 to about 5% by weight and preferably from about 0.10 to about 0.5% by weight of the composition. Trolox is a trademark of Hoffmann-LaRoche.

Furthermore, in accordance with the present invention, it has unexpectedly beer found that the Trolox C compound not only has antioxidant activity and antiinflammatory activity similar to that of Vitamin E, but that Trolox C by itself or formulated in skin treatment compositions in accordance with the present invention, has skin penetrating capacity which is surprisingly superior to that of Vitamin E. Accordingly, the skin treatment compositions of the invention contain a more skin penetrating form and thus a faster acting form of Vitamin E, that is Trolox C, than heretofore known.

In addition, there is provided a more stable form of Trolox C and a method for stabilizing Trolox C by employing Trolox C together with a stabilizer therefor, namely, sodium bisulfite or monoethanolamine sulfite and a method for stabilizing Trolox C against discoloration and oxidation by employing such stabilizer in composition with Trolox C.

A stabilized form of Trolox C in accordance with the present invention will comprise a stabilized composition containing from about 0.01 to about 5% Trolox C and preferably from about 0.1 to about 0.5% by weight Trolox C; and if necessary for solubility, an equivalent weight of strong base such as potassium hydroxide, sodium hydroxide, or lithium hydroxide (in an amount within the range of from about 0.02 to about 0.1% by weight) or organic amine, such as triethanolamine (in an amount within the range of from about 0.06 to about 0.3% by weight), from about 50 to about 90% and preferably from about 60 to aobut 80% by weight water; from about 0.05 to about 2% and preferably from about 0.1 to about 1% by weight preservative; and from about 0.02 to about 0.5% and preferably from abort 0.05 to about 0.1% by weight stabilizer which is sodium bisulfite or monoethanolamine sulfite which inhibits discoloration and oxidation of the Trolox C, all of the above % by weight being based on the weight of said stabilized composition.

In the above composition, the Trolox C will be employed in a molar ratio to the stabilizer of within the range of from about 10:1 to about 0.5:1 and preferably from about 5:I to about 1:1.

In addition, depending upon the form that the skin treatment composition of the invention will take, for example, moisturizing composition, skin toner, skin cleanser, night cream, day lotion, shampoo or cosmetic preparation, it will also include water, at least one preservative, preferably, at least one humectant, at least one emulsifier and/or thickener, and optionally may contain one or more chelating agents, one or more gelling agents, one or more emollients, one or more solvents for the free radical inhibitor or deactivator, one or more sun screen agents, and/or one more fragrances and/or one or more coloring agents.

The skin treatment composition of the invention is preferably an oil-in-water type emulsion since this type of emulsion affords better cosmetic feel to the product. However, the product could also be formulated as a water-in- oil emulsion, cream base, oil base or aqueous-/alcoholic or glycol solution, microemulsion or liposome. Depending upon the choice of ingredients, the formulation has a semi-solid cream-like consistency which can be packaged in a plastic squeeze tube, a lotion type consistency which can be packaged in a plastic squeeze container, an ointment-type consistency which can be packaged in a squeeze type container or a liquid consistency which may be packaged in a bottle. The container can include a flow-type cap or pump-type dispenser.

In addition, in accordance with the present invention, a method is provided for controlling free radical formation in skin, which includes the step of applying to the skin an effective amount of a skin treatment composition as disclosed herein.

The skin treatment composition of the invention may take the form of a lotion, cream, liquid, or ointment.

In general, regardless of the form of the skin treatment composition of the invention, it will include from about 0.01 to about 5%, and preferably from about 0.1 to about 0.5% by weight of the free radical inhibitor or deactivator, and, if necessary for solubility, an equivalent weight of caustic hydroxide, such as potassium hydroxide, (in an amount within the range of from about 0.02 to about 0.1% by weight) or organic amine, such as triethanolamine (in an amount within the range of from about 0.06 to about 0.3% by weight), from about 50 to about 90% and preferably from about 60 to about 80% by weight water, from about 1 to about 25% and preferably from about 5 to about 10% by weight of one or more humectants, from about 1 to about 10% and preferably from about 1 to about 5% by weight of one or more emulsifiers when the composition is a cream, lotion or ointment, from about 0.05 to about 4% and preferably from about 0.05 to about 3% by weight of one or more thickeners or gelling agents where the composition is a cream, lotion or ointment, optionally from about 0.001 to about 2% and preferably from about 0.01 to about 1% by weight of an enzyme or modified enzyme to enhance free radical inhibitor activity, optionally from about 0.01 to about 5% and preferably from about 1 to about 3% by weight of one or more adjuvant oxygen deactivators, from about 0.05 to about 2% and preferably from about 0.1 to about 1% by weight of one or more preservatives, and the following optional ingredients: from about 0.01 to about 0 5% and preferably from about 0.05 to about 0.1% by weight of one or more chelating agents, from about 1 to about 30% and preferably from about 1 to about 10% by weight of one or more emollients when the composition is a cream, lotion or ointment, from about 1 to about 50% and preferably from about 5 to about 10% by weight of one or more solvents for the free radical inhibitor or deactivator, from about 1 to about 15% and preferably from about 1.5 to about 10% by weight of one or more sun screen agents, less than about 1% by weight of one or more fragrances and/or less than about 1% by weight of one or more colorants. In addition, the skin treatment composition of the invention may also optionally include various other conventional ingredients normally employed in skin conditioning or moisturizing compositions or sunscreen compositions such as skin conditioning agents, moisturizers, waxes, polymers or other active ingredients.

Where the free radical inhibitor employed is Trolox C, the composition of the invention may optionally contain from about 0.02 to about 0.5% and preferably from about 0.05 to about 0.1% by weight stabilizer for the Trolox C.

The skin treatment composition of the invention may optionally contain enzymes of modified (PEG-, dextran PVP) enzymes to enhance acitivity, for example, polyethylene glycol modified superoxide dismutase or catalase. The composition may also optionally contain adjuvants to deactivate singlet oxygen or other active chemicals including but not limited to carotenoids (beta carotene, canthaxanthin, bixin), sulfur compounds (glutathione, cysteine, thioglycerol, dilaurylthiodiproprionate) or aromatic hydroxy or quinone compounds (e.g., quercetin, curcumin, hydroquinone) or vitamins (ascorbic acid, alpha-tocopherol).

Suitable preservatives include imidazolidinyl urea (Germall 115), methylparaben (Tegosept M), quaternium-15 (N-(3-chloroallyl)hexaminium chloride, Dowicil 200), propylparaben (Tegosept P), dimethyldimethoyl hydantoin, benzyl alcohol and/or phenoxyethanol, etc., and a preferred antioxidant is a mixture of butylated hydroxyanisole, propylene glycol, propyl gallate and citric acid (Tenox 2). The formulation will preferably contain the antioxidant mixture and one or more of the preservatives or any other preservatives and antioxidants approved for cosmetic use.

Where the skin treatment composition of the invention is in the form of a lotion, cream, or ointment, it will preferably including one or more emulsifiers, thickeners, humectants and emollients.

Suitable emulsifiers include polyethylene glycol 20 sorbitan monolaurate (Polysorbate 20), polyethylene glycol 5 soya sterol, sorbitan tristearate, sorbitan trioleate, glyceryl monopalmitate, diethanolamine cetyl phosphate, glyceryl monopalmitate, glyceryl monostearate, polyethylene glycol 100 stearate, polyethylene glycol 20 stearyl ether (Brij 78, teareth 20), polyethylene glycol ether of lauryl alcohol (Laureth 23), polysorbate 80 (Tween 80), lecithin, etc. The formulation will preferably contain a mixture of two or more of these emulsifiers or others which are approved for cosmetic use.

Thickeners or gelling agents which may be present include Carbopol 934 or Carbomer 940 which is a hydrophilic acrylic polymer cross-linked with a polyfunctional agent and employed with an organic or inorganic base, preferably triethanolamine. Other examples of thickeners which may be employed herein include, but are not limited to, stearic acid, fatty alcohols, such as cetyl alcohol, stearyl alcohol, magnesium aluminum silicate, stearoxydimethicone, hydroxyethyl cellulose, propylene glycol monostearate, hydroxypropyl cellulose, carboxymethyl cellulose, xanthan gum, myristyl stearate, or cetyl stearate.

Suitable emollients or oleaginous materials include mineral oil, petrolatum, glyceryl monooleate, myristyl alcohol, isopropyl palmitate, avocado oil, squalane, octyl palmitate, cocoa butter, sesame oil, propylene glycol dicaprylate/dicaprate, isopropyl myristate, diisopropyl dimerate (that is, the diester of isopropyl alcohol and dimer acid), dimethicone, stearoxydimethicone, and the like. The formulation will preferably contain a mixture of several of these emollients or others which are approved for cosmetic use.

Skin conditioning agents which may optionally be present in the composition of the invention include allantoin, d- or dl-panthenol, hydrolyzed animal protein and the like. Such conditioning agents may be present in an amount within the range of from about 0.01 to about 10% and preferably from about 0.05 to about 2% by weight and optimally from about 0.1 to about 2% by weight depending upon the ultimate use of the skin preparation.

Solvents for the free radical inhibitors which may be present include polyethylene glycol wax (such as Carbowax 400), propylene glycol or ethanol (for Trolox C) and/or an equivalent weight of strong base such as potassium hydroxide or organic amine such as triethanolamine (based on M.W. of Trolox C of 250.3), and mineral oil, vegetable oils, synthetic esters for ethoxyquin.

Chelating agents for sequestering metal ions in aqueous solution which may be present herein include disodium ethylenediamine tetraacetic acid, EDTA, tetrasodium EDTA, or citric acid.

As indicated, the skin treatment compositions of the invention may include one or more known ultraviolet absorbing agents, preferably at least one compound which absorbs in the UV-B region (wavelength 290 to 320 nanometers) and optionally one or more other compounds which absorb in the UV-A region (wavelength 320 to 400 nanometers). The total amount of UV absorbing agents included within the formulation will be from about 2% to about 15% by weight, which amount will determine whether it is a sunscreen or sunblock Suitable UV-A absorbing agents which may be employed include 2-(2'-hydroxy-5'-methylphenyl)benzotriazole (Tinuvin P); 2-(2'-hydroxy-5'-t-octylphenyl)-benzotriazole (Spectra-Sorb UV 5411); 2,4-dihydroxybenzophenone (Uvinul 400); 2-hydroxy-4-methoxybenzophenone (oxybenzone, Spectra-Sorb UV9, Uvinul M-40); 2,2',4,4'-tetrahydroxybenzophenone (Uvinul D50); 2,2'-dihydroxy-4,4'-dimethoxybenzophenone (Uvinul D49); 2,2'-dihydroxy-4-methoxybenzophenone (dioxybenzone, Spectra-Sorb UV24); 2-ethylhexyl-4-phenyl-benzophenone carbonate (Eusolex 3573); 2-hydroxy-4-methoxy-4'-methylbenzophenone (mexenone, Uvistat 2211); 2-hydroxy-4-(n-octyloxy)benzophenone (octabenzone, SpectraSorb UV531); 4-phenylbenzophenone (Eusolex 3490); and 2-ethylhexyl-2-cyano-3,3'-diphenylacrylate (Uvinul N539); butyl methoxydibenzoyl methane (Parsol 1789), and benzphthalide (Escalol 547). The UV-A absorbing agent or agents are present in the final product at from 0 to about 10% by weight of the formulation. The amount will vary according to the particular agent selected and whether the formulation is intended to minimize or permit tanning. Where a UV-A absorbing agent is employed, the preferred UV-A absorbing agent is 2-hydroxy-4-methoxybenzophenone alone or in combination with 2,2'-dihydroxy-4-methoxybenzophenone.

Suitable UV-B absorbing agents include 4-(dimethylamino)benzoic acid, ethyl ester; 4-(dimethylamino)-benzoic acid, 2-ethylhexyl ester (Escalol 507); 4-(dimethylamino)benzoic acid, pentyl ester (Escalol 506); glyceryl p-amino-benzoate (Excalol 106); isobutyl p-amino- benzoate (Cycloform); and isopropyl p-aminobenzoate; 2-ethylhexyl methoxy cinnamate (Parsol MCX); phenylbenzimidazole sulfonic acid (Eusolex 232); homomenthyl salicylate, and ethyl hexyl salicylate. The UV-B absoring agent or agents are present in the final product at from about 1% to about 15% by weight of the formulation. The amount will vary according to the particular agent selected and degree of protection desired in the final product. The preferred UV-B absorbing agent is 4-(dimethylamino)benzoic acid, 2-ethyl-hexyl ester (Escalol 507).

Where the skin treatment composition is in the form of a lotion, cream, or liquid, the free radical inhibitor or deactivator as well as any other actives that may be present will be "all-in-solution" (i.e., solubilized or emulsified) so that substantially no active ingredient crystallizes out at room temperature.

With regard to the cream formulations of the invention where the active ingredients are to be all- in-solution, the cream will contain from about 0.01 to about 5% and preferably from about 0.1 to about 0.5% by weight of the free radical inhibitor based on the weight of the entire cream formulation, and from about 1 to about 50% and preferably from about 5 to about 10% by weight of solvents for the free radical inhibitor based on the weight of the entire cream formulation. Examples of such solvents include Carbowax 400, propylene glycol, and/or an equivalent weight of strong base such as potassium hydroxide or organic amine such as triethanolamine (based on M.W. of Trolox C of 250.3) (for Trolox) and mineral oil or $C_{12}$–$C_{15}$ alcohols benzoate (for the ethoxyquin). The all-in-solution cream formulation will also include in the oil phase, from about 2 to about 15% and preferably from about 5 to about 10% by weight of the emulsifier-thickener based on the weight of the entire cream formulation, and from about 2 to 30% and preferably from about 3 to about 15% by weight of oleaginous material or emollient based on the weight of the entire cream formulation. The oil phase may also include one or more preservatives similar to that present in the aqueous phase described below.

The aqueous phase of the all-in-solution cream formulation may contain a glycol type preservative or humectant such as propylene glycol and/or a paraben or other conventional type perservative such methyl and/or propyl paraben, and purified water in amount within the range of from about 30 to about 80% by weight and preferably from about 35 to about 65% by weight of the entire cream formulation.

With regard to the lotion formulation of the invention where the free radical inhibitor is to be all-in-solution, the lotion will contain from about 0.01 to about 5% and preferably from about 0.1 to about 0.5% by weight of the free radical inhibitor based on the weight of the entire lotion formulation, and, if necessary, for solubility an equivalent amount of strong base such as potassium hydroxide or organic amine such as triethanolamine. The active ingredient in the all-in-solution lotion formulation can have part of it also solubilized in the oil phase. The lotion may contain from about 1 to 10% and preferably from about 2 to about 5% by weight emulsifierthickener based on the weight of the entire lotion formulation, and from about 2 to about 20% and preferably from about 4 to about 10% by weight of oleaginous material or emollient based on the weight of the entire lotion formulation. The oil phase may also optionally include one or more preservatives.

The aqueous phase of the all-in-solution lotion formulation may contain one or more preservatives and purified water in an amount within the range of from about 60 to about 90% by weight and preferably from about 70 to about 85% by weight of the entire lotion formulation.

Where the free radical inhibitor is to be employed in liquid solution, the concentration of free radical inhibitor will be in amounts ranging from about 0.01 to about 5% by weight together with from about 2 to about 99% by weight solvent therefor and, if necessary, for solubility, a strong base or organic amine as described hereinbefore.

The ointment formulation of the invention comprises a free radical inhibitor as described herein and an oleaginous material, and optionally a wax.

The term "ointment" or "ointment formulation" as employed herein includes non-aqueous formulations such as gels, ointments, lipophilic sticks, and the like.

The oleaginous material or emollient will generally be present in amount within the range of from about 30 to about 99% by weight, and preferably from about 50 to about 90% by weight.

The ointments of the invention may include the free radical inhibitor solubilized in both the aqueous phase and in the oil phase. The percentage of water in the aqueous phase may vary from about 5 to about 20% of the ointment.

The ointment will contain from about 0.01 to about 5%, and preferably from about 0.025 to about 0.5% by weight of the free radical inhibitor and from about 2 to about 99% by weight solvent therefor such as set out above. The all-in-solution ointment formulation (exclusive of the gel and lipophilic stick) will also include, in addition to the free radical inhibitor from about 85 to about 99% and preferably from about 85 to about 95% by weight of oleaginous material based on the weight of the entire formulation. The formulation may also optionally include an opacifying agent, such as titanium dioxide, serving as indicator for homogeneity of dispersion, in an amount within the range of from about 0.2 to about 1% and preferably from about 0.3 to about 0.8% by weight based on the entire formulation. When the free radical inhibitor is mechanically dispersed in the oleaginous material, the latter may be mineral oil thickened with polyethylene as disclosed in U.S. Pat. Nos. 2,627,938, 2,628,187, 2,628,205 and 3,733,403. The disclosures of the foregoing patents are incorporated herein by reference.

The all-in-solution ointment may simply be prepared by dissolving the active ingredient in a solvent therefor such as propylene glycol and/or polyethylene glycol wax (for Trolox) or $C_{12}$–$C_{15}$ alcohol benzoate (for ethoxyquin), with gentle heat not over 90° C., cooling to room temperature and then incorporating the same into the oleaginous material by slow mixing until homogeneous.

The gel formulation of the invention is preferably in the form of a lipophilic clear gel, and will contain from about 0.01 to about 5%, and preferably from about 0.1 to about 0.5% by weight of the free radical inhibitor based on the weight of the entire formulation, and from about 10 to about 99% and preferably from about 50 to about 80% by weight of a solvent for the free radical inhibitor (as described above) based on the weight of the entire formulation, depending upon the solubility of the particular inhibitor ingredient in the particular solvent employed. The gel formulation will also include from 30 to about 99% and preferably from about 60 to about 85% by weight of the oleaginous material. The formulation may also optionally include a surfactant, such as Span 65 (sorbitan tristearate), as well as Span 60 (sorbitan monostearate), Span 40 (sorbitan monopalmitate) or butylene glycol distearate in amounts up to about 8% by weight based on the entire formulation An antioxidant, such as butylated hydroxyanisole or butylated hydroxytoluene may also optionally be included in amounts up to about 0.1% and preferably up to about 0.05% by weight based on the entire formulation.

In the non-aqueous gel formulation of the invention, the oleaginous material includes mineral oil gelled with waxes such as high molecular weight paraffin wax (Paraflint RG), mono and diglycerides of fatty acids such as Arlacel 186 (Atlas Co.) as well as propylene glycol isostearate (Emery 2389A) or isostearyl alcohol (Adol 66), gelled with high molecular weight fatty acids such as Emery 865A (Emery Industries), and/or polyamide complex of hydroxystearate (Acrowax, Glyco).

The lipophilic stick of the invention may contain from about 0.01 to about 5%, and preferably from about 0.1 to about 0.5% by weight free radical inhibitor and from about 10 to about 80% and preferably from about 40 to about 60% by weight of the solvent therefor (such as described above) and from about 20 to 50% and preferably from about 25 to about 45% by weight oleoginous material. Oleoginous materials which may be employed include high melting waxes, such as carnauba wax, in amounts ranging from about 6 to about 10 and preferably about from about 7 to about 9%, beeswax in amounts ranging from about 14 to about 18% and preferably from about 15 to about 17%, as well as petrolatum in amounts ranging from about 2 to about 5% and preferably from about 3 to about 4%, and isotearyl neo pentanoate (Ceraphyl 375, Van Dyk) in amounts ranging from about 8 to about 11% and preferably from about 9 to about 10.5%.

In the case of ointments, lipophilic gels and sticks where the formulation is substantially free of water, the free radical inhibitor will be dissolved in the solvent vehicle and, in part, in the oil material employed.

Examples of preferred formulations in accordance with the present invention include, but are not limited to, the following:

|  | Range in % by weight |
| --- | --- |
| Cream formulation | |
| Free radical inhibitors | 0.1 to 0.5 |
| Stabilizer for Trolox C | 0 to 0.1 |
| Solvents for inhibitors (including neutralizing bases) | 5 to 10 |
| Emulsifiers | 2 to 5 |
| Thickeners | 2 to 20 |
| Humectant | 2 to 20 |
| Chelating Agent | 0.05 to 0.1 |
| Water | 50 to 80 |
| Preservatives | 0.2 to 1 |
| Lotion formulation | |
| Free radical inhibitors | 0.1 to 0.5 |
| Stabilizer for Trolox C | 0 to 0.1 |
| Solvents for inhibitors (including neutralizing bases) | 5 to 10 |
| Emulsifiers | 1 to 5 |
| Thickeners | 1 to 10 |
| Humectants | 2 to 10 |
| Chelating Agents | 0.05 to 0.1 |
| Water | 60 to 90 |
| Preservatives | 0.2 to 1 |
| Ointment formulation | |
| Free radical inhibitors | 0.1 to 0.5 |
| Stabilizer for Trolox C | 0 to 0.1 |
| Solvents for inhibitors (including neutralizing bases) | 5 to 80 |
| Oleagnous materials | 20 to 90 |
| Emulsifiers or thickeners | 10 to 30 |

-continued

| Solution or Liquid formulation | Range in % by weight |
|---|---|
| Free radical inhibitors | 0.1 to 0.5 |
| Stabilizer for Trolox C | 0 to 0.1 |
| Solvents for inhibitors (including neutralizing bases) | 5 to 10 |
| Water | 75 to 90 |

The various formulations of the invention may be prepared employing conventional procedures as outlined in the working Examples.

EXAMPLE 1

A skin treatment (moisturizer) composition in the form of a lotion of the following composition was prepared as described below.

| Ingredient | Parts by Weight |
|---|---|
| Blend I | |
| Deionized water | 74.1 |
| Disodium ethylenediamine tetraacetic acid (Sequestrene Na$_2$ - chelating agent) | 0.05 |
| (Carbopol 934, gellant-thickener) | 0.3 |
| Blend II | |
| Propylene glycol (solvent, humectant) | 5 |
| Benzyl alcohol (preservative) | 0.5 |
| Methyl paraben (preservative) | 0.15 |
| Blend III | |
| PEG 5 soya sterol (Generol 122E5-emulsifier) | 2 |
| PEG ether of lauryl alcohol (Laureth 23-emulsifier) | 2 |
| Glyceryl monostearate (Tegin 90, emulsifier, thickener) | 1 |
| Cetyl alcohol (thickener) | 0.5 |
| Stearic acid (thickener) | 1.25 |
| Diisopropyl dimerate (diester of isopropyl alcohol and dimer acid-emollient) | 5 |
| Dimethicone (Silicone 225, emollient) | 1 |
| Stearoxydimethicone (Silicone wax 755-emollient-bodying agent) | 1 |
| Propyl paraben (preservative) | 0.1 |
| Butyl paraben (preservative) | 0.05 |
| 6-Ethoxy-1,2-dihydro-2,2,4-trimethylquinoline (Santoquin-free radical inhibitor) | 0.1 |
| Triethanolamine (Carbopol neutralizer) | 0.4 |
| Deionized water | 0.4 |
| Blend IV | |
| Polyethylene glycol (Carbowax 400, humectant, solvent for Trolox) | 5 |
| 6-Hydroxy-2,5,7,8-tetramethyl-chroman-2-carboxylic acid (Trolox C-free radical inhibitor) | 0.1 |

Aqueous Blend I was prepared by dispersing the ingredients in the deionized water. Blend II (prepared by simple mixing of ingredients) was then mixed with Blend I. The combined Blend I-II was then heated to 75° C.

Blend III was formed by simple mixing of the ingredients in a separate vessel while heating to 75° C.

Blend III (heated at 75° C.) was then added to the combined Blend I-II (also at 75° C.) with sweep mixing.

The combined Blend I-II-III was heated at 75° C. for 30 minutes, allowed to air cool to 60° C., and then Blend IV (prepared by simple mixing of ingredients) was added with sweep mixing. The resulting batch was then allowed to air cool to 30° C. to form the moisturizer lotion formulation of the invention.

EXAMPLE 2

Topical Cream Moisturizer, 0.1% (all-in-solution)

| | |
|---|---|
| 6-Hydroxy-2,5,7,8-tetramethyl-chroman-2-carboxylic acid (Trolox C) (free radical inhibitor) | 0.1 gm. |
| Polyethylene glycol (Carbowax 400, solvent) | 5 gm. |
| Petrolatum, U.S.P. | 16.0 gm. |
| Promulgen, Type D (Cetearyl alcohol & Ceteareth-20), Amerchol | 8.0 gm. |
| Methylparaben | 0.15 gm. |
| Propylparaben | 0.02 gm. |
| Purified Water, sufficient to make | 100.0 gm. |

A solution of Trolox and polyethylene glycol is formed by gentle heating of a mixture thereof at not over 90° C. The parabens are then dissolved in the Trolox and polyethylene glycol solution with gentle heat, not over 90° C. Petrolatum and Promulgen D are melted together. After mixing, the mixture is added to the solution with thorough mixing, maintaining the temperature at 75°–80° C. Water is heated to 80° C. to form the aqueous phase which is added with vigorous agitation to the oil phase to emulsify Agitation is continued until the temperature drops down to 48° C. Sufficient 50° C. water is added to make 100 gm. Mixing is continued at a slow rate to congeal the mixture, until the temperature drops to 30° C.

EXAMPLE 3

Ointment, 0.1% (all-in solution)

| | |
|---|---|
| 6-Ethoxy-1,2-dihydro-2,2,4-trimethylquinoline (Santoquin-free radical inhibitor) | 0.1 gm. |
| (Solvent) C$_{12}$—C$_{15}$ alcohols benzoate | 5 gm. |
| Titanium Dioxide | 0.5 gm. |
| Plastibase 50W (mineral oil) (95%) gelled with polyethylene (5%) sufficient to make 100.0 gm. | |

The free radical inhibitor is dissolved with gentle heat not over 90° C. The solution is cooled to room temperature and titanium dioxide is dispersed homogeneously into the oil. The suspension is incorporated into the Plastibase by slow rate of mixing until homogeneous to form the ointment.

EXAMPLE 4

Lipophilic Gel, 0.1% (all in solution)

| | |
|---|---|
| 6-Hydroxy-2,5,7,8-tetramethyl-chroman-2-carboxylic acid (Trolox) (free radical inhibitor) | 0.1 gm. |
| Polyethylene glycol (carbowax 400) | 1 gm. |
| Mineral Oil, U.S.P. | 80.375 gm. |
| Parflint RG (High melting paraffin wax), Moore and Munger | 6.0 gm. |
| Span 65 (Sorbitan tristearate, ICI) | 3.6 gm. |

Paraflint RG and Span 65 are melted and heated to 100° C. The molten mixture is incorporated in hot (100° C.) mineral oil and mixed well. The temperature of the oil is quickly brought to 50° C. to form a gel.

The free radical inhibitor is dissolved in the polyethylene glycol by gentle heat, the oil is cooled to room temperature and then is incorporated in the gel homogeneously.

EXAMPLE 5

A sunscreen oil-in-water formulation in the form of a lotion having the following composition is prepared as described below

| Ingredient | Parts by Weight |
| --- | --- |
| Blend I | |
| Deionized water | 68 |
| Magnesium aluminum silicate (Veegum R, thickener) | 0.5 |
| Triethanolamine (99%) | 0.1 |
| Blend II | |
| Polyethylene glycol 400 (humectant) | 5 |
| Methyl paraben (Tegosept M, preservative) | 0.2 |
| Xanthan gum (Keltol F, thickener) | 0.2 |
| 6-Hydroxy-2,5,7,8-tetramethylchroman-2-carboxylic acid (Trolox C-free radical inhibitor) | 0.1 |
| Blend III | |
| Polyethylene glycol stearyl ether (Brij 78, emulsifier) | 1 |
| Cetyl alcohol (thickener, emollient) | 0.5 |
| Stearic acid (thickener) | 2 |
| Propylparaben (Tegosept P, preservative) | 0.1 |
| Butylparaben (Tegosept B, preservative) | 0.1 |
| Polyethylene glycol 100 stearate and glycerol monostearate (1:1) (Arlacel 165, emulsifier) | 2 |
| C$_{12}$—C$_{15}$ alcohol benzoate (Finsolv TN, emollient) | 2 |
| Polyethylene glycol 5 soya sterol (Generol 122 E5, emollient, emulsifier) | 0.5 |
| Cetearyl octanoate (Purcellin oil, emollient) | 4 |
| 4-(Dimethylamino)benzoic acid, 2-ethylhexyl ester (Escalol 507, sunscreen, UV-B) | 2 |
| Blend IV | |
| Deionized water | 10 |
| Troxerutin (tri(hydroxyethyl)rutoside) (sun protection) | 1 |
| Blend V | |
| Chloroallyl methenamine chloride (Dowicil 200, preservative) | 0.1 |
| Deionized water | 0.5 |

Aqueous Blend I is prepared by mixing the thickener ingredients in the deionized water. Blend II, prepared by simple mixing of ingredients, is then mixed with Blend I. The combined Blends I-II is then heated to 75° C.

Blend III is formed by simple mixing of the ingredients in a separate vessel while heating at 75° C.

Blend III (heated at 75° C.) is then added to the combined Blend I-II (also at 75° C.) with sweep mixing.

The combined Blend I-II-III was heated at 75° C. for 30 minutes, allowed to air cool to 60° C. and then Blends IV and V each formed by simple mixing of ingredients are separately added with sweep mixing.

The resulting batch is then allowed to air cool to 30° C. to form the sunscreen formulation of the invention.

EXAMPLE 6

A protective daytime lotion/moisturizer having the following composition is prepared as described below.

| Ingredient | Parts by Weight |
| --- | --- |
| Mix A | |
| Deionized water (diluent) | 74 |
| Magnesium aluminum silicate (thickener stabilizer) | 0.5 |
| dl-Panthenol (skin protecting agent) | 1 |
| Monoethanolamine sulfite (stabilizer) | 0.1 |
| Mix B | |
| Troxerutin | 1 |
| Octyl dimethyl p-aminobenzoic acid (sunscreen) | 2 |
| Diisopropyl dimerate (emollient oil) | 4 |
| Propylene glycol dicaprylate/dicaprate (emollient oil) | 8 |
| Propyl paraben (preservative) | 0.1 |
| Stearic acid (opacifier, bodying agent) | 3 |
| Brij 78 (Steareth 20) (emulsifier) | 2 |
| Glyceryl stearate and PEG 100 stearate (emulsifier, thickener) | 3 |
| Mix C | |
| Carbowax 400 (PEG 8) (humectant) | 3 |
| Xanthan gum (thickener, stabilizer) | 0.1 |
| Methyl paraben (preservative) | 0.2 |
| 6-Hydroxy-2,5,7,8-tetramethylchroman-2-carboxylic acid (Trolox C-free radical inhibitor) | 0.3 |
| Triethanolamine (99%) | 0.2 |
| Mix D | |
| Glydant (dimethyldimethoyl hydantoin) (preservative) | 0.4 |

Each of Mixes A and B are heated to 75° C. and Mix B is added to Mix A with propeller type mixing while maintaining the 75° C. temperature for 1 hour. The resulting mixture is cooled to 65° C. and Mix C is added. The mixture is then cooled to 50° C. and Mix D is added. Cooling is continued to 30° C. to form the protective daytime lotion/ moisturizer of the invention which is found to have improved feel and barrier properties, is naturally compatible with the skin and has improved skin penetrability.

EXAMPLE 7

A soothing facial make-up having the following composition is prepared as described below.

| Ingredient | Parts by Weight |
| --- | --- |
| Phase A | |
| Deionized water | 48 |
| Veegum R (magnesium aluminum silicate) (thickener) | 1 |
| Phase B | |
| Kaolin 2749 (skin protectant) | 4 |
| Umber 1985R | 0.5 |
| Russet C33-2527 | 0.3 |
| Yellow 2576 | 1 |
| Blue 3516 | 0.01 |
| Phase C | |

| Ingredient | Parts by Weight |
|---|---|
| TiO₂ water dispersable (90% TiO₂, 10% Talc) | 10 |
| Phase D | |
| Alcolec 413S (lecithin and Polysorbate 20 and sorbitan laurate and propylene glycol stearate and propylene glycol laurate) | 1 |
| Phase E | |
| Deionized water | 1 |
| dl-Panthenol (skin protectant) | 0.5 |
| Phase F | |
| Carbowax 400 (humectant) | 4.5 |
| Tegosept P (propyl paraben) (preservatives) | 0.2 |
| Keltrol F (xanthan gum) (thickener) | 0.2 |
| 6-Hydroxy-2,5,7,8-tetramethylchroman-2-carboxylic acid (Trolox C-free radical inhibitor) | 0.5 |
| Phase G | |
| Deionized water | 2 |
| Triethanolamine (96%) (emulsifier) | 1 |
| Monoethanol amine sulfite (stabilizer) | 0.2 |
| Phase H | |
| Tegosept P (propyl paraben) (preservative) | 0.1 |
| Butoben (butyl paraben) (preservative) | 0.1 |
| Klearol (mineral oil) (emollient) | 5 |
| Miglyol 840 (propylene glycol dicaprylate/tricaprate) (emollient) | 6 |
| Stearic acid (emulsifier, thickener) | 3.5 |
| Tegin 515 (glyceryl monostearate) (auxiliary emulsifier, thickener) | 2.5 |
| Escalol 507 (octyl dimethyl p-amino benzoic acid) (sunscreen) | 2.5 |
| Uvinol M-40 (benzophenone 3) (sunscreen) | 0.5 |
| Troxerutin | 1 |
| Silicone 225 (emollient) | 1.5 |
| Avocado oil (emollient) | 0.5 |
| PEG-6000 distearate (emulsifier thickener) | 0.2 |
| Vitamin E, dl alpha-tocopherol (antioxidant) | 0.1 |
| Phase I | |
| Deionized water | 0.75 |
| Germall 115 (preservative) | 0.25 |
| Phase J | |
| Carbowax 400 (humectant) | 0.5 |
| Exaltolide (pentadecalactone) (odor masking agent) | 0.5 |

The Phase A ingredients are homomixed for 15 minutes. Thereafter, a mix of the Phase B ingredients are added to the Phase A mixture with mixing for 1 hour. Phase C is then mixed with Phase AB for ½ hour under slow speed mixing. Phase D is then added to the aforementioned mix with mixing for ½ hour. Phase E is then added and thereafter Phase F is sweep mixed therein for 15 minutes. The so-formed mix is then heated to 75° C. While maintaining the mix at 75° C., Phase G is added. Phase H, heated at 80° C., is then added to the above mix with fast mixing to form an emulsion. The mix is then mixed with moderate speed, cooled to 50° C. and then combined with Phase I and mixed for 5 minutes. Thereafter Phase J is added and the mixture is cooled to 30° C. to form the make-up of the invention. The so-formed make-up of the invention is found to be soothing and noncomedongenic.

EXAMPLE 8

Cosmetic Formulation

A cosmetic formulation in the form of a facial makeup having the following composition is prepared as described below.

| Ingredient | Grams |
|---|---|
| Deionized water | 76 |
| Glycerin | 4.5 |
| 2-Pyrrolidone-5-carboxylic acid (PCA) | 0.6 |
| Methyl paraben | 0.2 |
| Ceraphyl 368 (octyl palmitate) | 3 |
| Silicone 225 (dimethicone) | 1 |
| Tween 60 (Polysorbate 60) | 4.5 |
| Propyl paraben | 0.1 |
| Tegin 515 (glyceryl monostearate 40% mono) | 2 |
| Promulgen D (cetearyl alcohol + ceteareth 20) | 5.5 |
| Deionized water | 0.5 |
| Dowicil 200 (Quaternium 15) | 0.1 |
| 6-Hydroxy-2,5,7,8-tetramethylchroman-2-carboxylic acid (Trolox C-free radical inhibitor) | 0.2 |

Glycerin, 2-pyrrolidone-5-carboxylic acid and methyl paraben are heated together to 70° to 75° C. with propeller mixing to form a first mix.

Octyl palmitate, dimethicone, polysorbate 60, propyl paraben, glyceryl monostearate and Promulgen D (cetearyl alcohol and Cetearth 20) are heated together to 70° to 75° C. with propeller mixing to form a second mix.

The second mix is then added to the first mix with propeller mixing and the mixture is then cooled to 60° C. while sweep mixing. Thereafter, aqueous Dowicil 20 (Quaternium 15) and Trolox C are added at 50° C. and the mixture is cooled to 30° C. to form the cosmetic of the invention.

EXAMPLE 9

Shampoo Formulation

A shampoo having the following composition is prepared as described below.

| Ingredient | Grams |
|---|---|
| Deionized water | 50 |
| Standapol ES2 (25% sodium laureth 2-sulfate) | 40 |
| Glydant (55% solution dimethyl dimethoyl hydantoin) | 0.3 |
| Standapol AB 45% (45% lauryl betaine) | 5 |
| Perfume oil | 0.5 |
| Triton X102 (octoxyonol 13) | 2 |
| Methyl paraben | 0.1 |
| FDC Red 4 (0.1% solution) | 0.05 |
| 85% Phosphoric acid | (qs to pH 6.0) |
| Troxerutin | 1 |
| 6-Hydroxy-2,5,7,8-tetramethylchroman-2-carboxylic acid (Trolox C-free radical inhibitor) | 0.1 |
| Potassium hydroxide | 0.05 |

A first mix is formed by sweep mixing deionized water, Standapol ES2, Glydant and Standapol AB 45% while heating to 60°-65° C. THe first mix is cooled to 50° C. and then perfume oil, Triton X102, Tegin and the FD&C color are added to the first mix with sweep mixing to form a second mix. The pH of the second mix is adjusted to 6.0 with phosphoric acid, at 50° C. and then the troxerutin and Trolox C and KOH are added at 50° C. and the mix is cooled to 30° C. to form the shampoo formulation of the invention.

EXAMPLE 10

Topical Moisturizer Lotion Composition

A topical moisturizer lotion having the following composition is prepared as described below

|  | Parts by Weight |
|---|---|
| Blend I | |
| Carboxymethyl cellulose | 1 |
| Carbowax 400 | 2 |
| Deionized water | 47 |
| Blend II | |
| Glydant | 0.3 |
| Imidizolidinyl urea | 0.2 |
| Deionized water | 1 |
| Blend III | |
| Carbowax 400 | 10 |
| 6-Hydroxy-2,5,7,8-tetramethylchroman-2-carboxylic acid (Trolox C-free radical inhibitor) | 0.5 |
| Triethanolamine (99%) | 0.3 |
| Blend IV | |
| Tween 80 (Polysorbate 80) | 2.2 |
| Tween 20 (Polysorbate 20) | 0.6 |
| Blend IV | |
| Monoethanolamine sulfite (stabilizer for Trolox C) | 0.2 |
| Deionized water | 34.3 |

Blend I was formed by premixing the carboxymethyl cellulose and Carbowax 400 and adding the water under homomixing while heating at 50° C.

The Blend II ingredients were mixed together and added to Blend I to form Blend I-II.

The Blend III ingredients were stirred at 80° C. until uniform and the resulting Blend III was sweep mixed into Blend I-II to form Blend I-II-III.

Blend IV and V ingredients were then sweep mixed as two separate blends into the Blend I-II-III to form the final blend.

The so-formed topical moisturizer lotion of the invention was found to have excellent moisturizing properties and excellent skin penetrating power.

In addition, the Trolox C free radical inhibitor was found to be stabilized against decoloration and oxidation by the monoethanolamine sulfite.

What is claimed is:

1. A skin treatment composition which inhibits generation of or deactivates the free radicals in the skin which free radicals may form upon exposure of the skin to ultraviolet radiation or air pollutants, in the form of an ointment, cream, lotion, or liquid comprising water, at least one humectant, at least one thickener, at least one preservative and from about 0.01 to about 5% by weight of the composition of at least one free radical inhibitor or deactivator which is 6-hydroxy-2,5,7,8-tetra-methylchroman-2-carboxylic acid, 6-ethoxy-1,2-dihyro-2,2,4-trimethylquinoline or mixtures thereof.

2. The composition as defined in claim 1 wherein the free radical inhibitor or deactivator of claim 1 is present in an amount within the range of from about 0.1 to about 0.5% by weight of the composition.

3. The composition as defined in claim 1 wherein the free radical inhibitor or deactivator is 6-hydroxy-2,5,7,8-tetramethylchroman-2-carboxylic acid.

4. The composition as defined in claim 3 wherein the humeotant is propylene glycol, polyethylene glycol, glycerine, sorbitol or butylene glycol.

5. The composition as defined in claim 1 wherein the free radical inhibitor or deactivator is 6-ethoxy,-1,2-dihydro-2,2,4-trimethylquinoline.

6. The composition as defined in claim 1 further including a chelating agent which is disodium ethylene diamine tetraacetic acid, tetrasodium EDTA or citric acid.

7. The composition as defined in claim 1 in the form of a cream, lotion or ointment, wherein the thickener is a cross-linked acrylic acid polymer and including triethanolamine as a neutralizer for said thickener, or said thickener is xanthan gum, magnesium aluminum silicate, hydroxyethyl cellulose, carboxymethyl cellulose, cetyl alcohol or stearic acid.

8. The composition as defined in claim 1 further including an emulsifier.

9. The composition as defined in claim 8 wherein the emulsifier is polyethylene glycol 20 sorbitan monolaurate, polyethylene glycol 5 soya sterol, sorbitan tristearate, sorbitan trioleate, glyceryl monopalmitate, diethanolamine cetyl phosphate, glyceryl monostearate, polyethylene glycol 100 stearate, polyethylene glycol 20 stearyl ether, polyethylene glycol ether of lauryl alcohol, polysorbate 80, lecithin or mixtures thereof.

10. The composition as defined in claim 1 further including an emollient.

11. The composition as defined in claim 11 wherein the emollient is dimethicone, stearoxydimethicone, diisopropyl dimerate or mineral oil.

12. The composition as defined in claim 1 wherein the preservative is benzyl alcohol, phenoxyethanol, butyl paraben, propylparaben, methyl paraben, imidazolidinyl urea, dimethyldimethoyl hydantoin, or a mixture thereof.

13. The composition as defined in claim 1 further including a solvent for the free radical inhibitor or deactivator.

14. The composition as defined in claim 1 wherein the solvent is propylene glycol, polyethylene glycol, ethanol and/or strong base or organic amine for 6-hydroxy-2,5,7,8 tetraethylchroman-2-carboxylic acid and vegetable oil or synthetic fatty acid esters for 6-ethoxy-1,2-dihydro-2,2,4-trimethyl quinoline.

15. The composition as defined in claim 1 wherein the free radical inhibitor or deactivator is present in an amount within the range of from about 0.1 to about 0.5% by weight and is 6-hydroxy-2,5,7,8-tetramethylchroman-2-carboxylic acid and 6-ethoxy-1,2-dihydro-2,2,4-trimethylquinoline, the humectant is polyethylene glycol and propylene glycol, the emulsifier or thickener is polyethylene glycol 5 soya sterol, polyethylene glycol ether of lauryl alcohol, glyceryl monostearate, cetyl alcohol or stearic acid, and the preservative is benzyl alcohol, methyl paraben, propyl paraben or butylparaben.

16. The composition as defined in claim 15 further including disodium ethylenediamine tetracetic acid as a chelating agent, diisopropyl dimerate, dimethicone and stearoxy dimethicone as an emollient, and polyethylene glycol as a solvent for 6-hydroxy-2,5,7,8-tetramethylchroman2-carboxylic acid.

17. The composition as defined in claim 1 further including at least one enzyne or modified enzyme.

18. The composition as defined in claim 1 further including at least one adjuvant oxygen deactivator.

19. A skin treatment composition which inhibits generation of or deactivates the free radicals in the skin which free radicals may form upon exposure of the skin to ultraviolet radiation or air pollutants, in the form of an ointment, cream, lotion, or liquid comprising water, at least one humectant, at least one thickener, at least one preservative, at least one chelating agent which is disodium ethylene diamine tetraacetic acid, ethylene diamine tetraacetic acid, tetrasodium ethylene diamine tetraacetic acid or citric acid and from about 0.01 to about 5% by weight of the composition of at least one free radical inhibitor or deactivator which is 6-hydroxy-2,5,7,8-tetra- methylchroman-2-carboxylic acid, 6-ethoxy-1,2-dihyro-2,2,4-trimethylquinoline or mixtures thereof.

20. A skin treatment composition which inhibits generation of or deactivates the free radicals in the skin which free radicals may form upon exposure of the skin to ultraviolet radiation or air pollutants, in the form of an ointment, cream, lotion, or liquid comprising water, at least one humectant, at least one enzyme or modified enzyme, at least one thickener, at least one preservative and from about 0.01 to about 5% by weight of the composition of at least one free radical inhibitor or deactivator which is 6-hydroxy-2,5,7,8-tetra- methylchroman-2-carboxylic acid, 6-ethoxy-1,2-dihyro-2,2,4-trimethylquinoline or mixtures thereof.

21. The composition as defined in claim 20 wherein the enzyme is glycol modified superoxide dismutase or catalase.

22. A method for controlling free radical formation on skin which comprises applying to the skin of a mammalian in need of such treatment an effective amount of a skin treatment composition in the form of an ointment, cream, lotion or liquid comprising water and from about 0.01 to about 5% by weight of a free radical inhibitor or deactivator which is 6-hydroxy-2,5,7,8-tetramethylchroman-2-carboxylic acid, 6-ethoxy-1,2-dihydro-2,2,4-trimethylquinoline, or mixtures thereof.

* * * * *

UNITED STATES PATENT AND TRADEMARK OFFICE
CERTIFICATE OF CORRECTION

PATENT NO. : 4,970,216

DATED : November 13, 1990

INVENTOR(S) : Deckner et al.

It is certified that error appears in the above-identified patent and that said Letters Patent is hereby corrected as shown below:

In the Abstract, line 4, "2,3,4-trimethyl" should read --2,2,4-trimethyl--.
Column 1, line 55, "hydroxy2," should read --hydroxy-2,--.
Column 2, line 15, "beer" should read --been--.
Column 2, line 44, "aobut" should read --about--.
Column 2, line 47, "abort" should read --about--.
Column 2, line 56, "5:I" should read --5:1--.
Column 2, line 67, between "one more", insert --or--.
Column 3, line 52, "05%" should read --0.5%--.
Column 4, line 33, "including" should read --include--.
Column 4, line 41, "teareth" should read --Steareth--.
Column 5, line 31, after "sunblock" insert --.--.
Column 5, line 34, "(2'-hydroxy-5'-t-octylphenyl)" should read --(2'-hydroxy-5'-t-octyl-phenyl)--.
Column 5, line 44, "2-hydroxy-4-(n-octyloxy)" should read --2-hydroxy-4-(n-octyloxy)--.
Column 5, line 62, "Excalol" should read --Escalol--.
Column 5, line 66, "ethyl hexyl" should read --ethylhexyl--
Column 6, line 5, "2-ethyl-hexyl" should read --2-ethylhexyl--.
Column 6, bridging lines 56-57, "emulsifierthickener" should read --emulsifier-thickener--.
Column 8, line 2, between "formulation An", insert --.--.
Column 8, line 23, "oleoginous" should read --oleaginous--.
Column 8, line 26, "10and" should read --10% and--.
Column 8, line 31, "isotearyl" should read --isostaryl--.
Column 8, in the table, line 30, "Oleagnous" should read --oleaginous--.
Column 9, in Example 1, under the heading Blend II, "humectant" should read --humectant)--.

UNITED STATES PATENT AND TRADEMARK OFFICE
CERTIFICATE OF CORRECTION

PATENT NO. : 4,970,216

DATED : November 13, 1990

INVENTOR(S) : Deckner et al.

It is certified that error appears in the above-identified patent and that said Letters Patent is hereby corrected as shown below:

```
Column 10, line 30, between "emulsify Agitation", insert
--.--.
Column 10, in Example 4, "Parflint" should read
--Paraflint--.
Column 14, line 64, "THe" should read --The--.
Column 15, bridging lines 59 and 60, "tet-ra-methylchroman"
sould read --tetramethylchroman--.
Column 16, line 2, "humeotant" should read --humectant--.
Column 16, line 5, "6-ethoxy,-1,2-" should read --6-ethoxy-
1,2- --.
Column 16, line 44, "tetraethylchroman" should read --
tetramethylchroman--.
Column 16, line 64, "chroman2" should read --chroman-2--.
Column 17, line 13, "tetra- methylchroman" should read --
tetramethylchroman--.
Column 18, line 5, "tetra- methylchroman" should read --
tetramethylchroman--.
```

Signed and Sealed this

Ninth Day of June, 1992

*Attest:*

DOUGLAS B. COMER

*Attesting Officer*     Acting Commissioner of Patents and Trademarks